US011083677B2

(12) United States Patent
Inoue et al.

(10) Patent No.: US 11,083,677 B2
(45) Date of Patent: Aug. 10, 2021

(54) COSMETIC BASE INCLUDING AMIDE ALCOHOL, AND COSMETIC

(71) Applicant: Kokyu Alcohol Kogyo Co., Ltd., Narita (JP)

(72) Inventors: Takanori Inoue, Narita (JP); Mari Masuno, Narita (JP)

(73) Assignee: Kokyu Alcohol Kogyo Co., Ltd., Narita (JP)

( * ) Notice: Subject to any disclaimer, the term of this patent is extended or adjusted under 35 U.S.C. 154(b) by 0 days.

(21) Appl. No.: 16/308,180

(22) PCT Filed: Jun. 7, 2017

(86) PCT No.: PCT/JP2017/021154
§ 371 (c)(1),
(2) Date: Aug. 6, 2019

(87) PCT Pub. No.: WO2017/213177
PCT Pub. Date: Dec. 14, 2017

(65) Prior Publication Data
US 2019/0343745 A1    Nov. 14, 2019

(30) Foreign Application Priority Data

Jun. 8, 2016 (JP) .............................. JP2016-114276

(51) Int. Cl.
*A61K 8/42* (2006.01)
*A61Q 5/10* (2006.01)
*A61Q 5/12* (2006.01)
*A61Q 19/00* (2006.01)

(52) U.S. Cl.
CPC ................ *A61K 8/42* (2013.01); *A61Q 5/10* (2013.01); *A61Q 5/12* (2013.01); *A61Q 19/00* (2013.01); *A61K 2800/48* (2013.01)

(58) Field of Classification Search
CPC .. A61K 31/706; A61K 9/0019; A61K 9/0073; A61K 31/727; A61K 31/352; A61K 31/13; A61K 31/7072; A61K 31/522; A61K 31/7064; A61K 31/513; A61K 31/4045; A61K 31/7056; A61K 47/06; A61K 9/0053; A61K 31/365; A61K 31/551; A61K 45/06; A61K 8/42; A61K 2800/48; A61P 31/14; A61M 2205/05; A61M 1/3496; A61M 1/16; A61M 2202/0208; A61M 1/1698; A61F 9/00; A61Q 5/10; A61Q 5/12; A61Q 19/00; A61Q 19/005; A61Q 5/065; A61Q 19/007; C09K 3/00
See application file for complete search history.

(56) References Cited

U.S. PATENT DOCUMENTS

| | | | |
|---|---|---|---|
| 3,125,530 | A | 3/1964 | Mayhew et al. |
| 3,792,082 | A | 2/1974 | Loiseau et al. |
| 4,143,159 | A | 3/1979 | Moller et al. |
| 4,325,973 | A | 4/1982 | Graham et al. |
| 4,749,563 | A | 6/1988 | Georgalas |
| 5,089,175 | A | 2/1992 | Earnshaw et al. |
| 5,750,096 | A | 5/1998 | Guskey |
| 2002/0159961 | A1 | 10/2002 | Yamato et al. |
| 2004/0229984 | A1 | 11/2004 | Yamato et al. |
| 2007/0237732 | A1 | 10/2007 | Yamato et al. |
| 2008/0145320 | A1 | 6/2008 | Wenk et al. |
| 2011/0251294 | A1 | 10/2011 | Weiss et al. |

FOREIGN PATENT DOCUMENTS

| | | |
|---|---|---|
| GB | 1 525 449 A | 9/1978 |
| GB | 1554251 | 10/1979 |
| JP | S53-38637 | 4/1978 |
| JP | S53-38637 A | 4/1978 |
| JP | H01-502116 A | 7/1989 |
| JP | H03-505216 A | 11/1991 |
| JP | 07-126233 A | 5/1995 |
| JP | H07-118290 A | 5/1995 |
| JP | H07-126233 A | 5/1995 |
| JP | 07-258689 A | 10/1995 |
| JP | H07-258689 A | 10/1995 |
| JP | 07-310093 A | 11/1995 |
| JP | H07-310093 A | 11/1995 |
| JP | H08-503478 A | 4/1996 |
| JP | 8-283139 A | 10/1996 |
| JP | 2000-504036 A | 4/2000 |
| JP | 2001-507039 A | 5/2001 |
| JP | 2002-316971 A | 10/2002 |
| JP | 2003-300846 A | 10/2003 |
| JP | 2005-60457 A | 3/2005 |
| JP | 2005-060457 A | 3/2005 |
| JP | 2005-255777 A | 9/2005 |
| JP | 2008-120811 A | 5/2008 |
| JP | 2015-067571 A | 4/2015 |
| JP | 2015-67571 A | 4/2015 |
| WO | WO 88/04167 A1 | 6/1988 |
| WO | WO 94/12467 A1 | 6/1994 |

(Continued)

OTHER PUBLICATIONS

PCT/JP2017/021154, Jul. 11, 2017, International Search Report and Written Opinion.

(Continued)

*Primary Examiner* — Robert S Cabral

(74) *Attorney, Agent, or Firm* — Wolf, Greenfield & Sacks, P.C.

(57) ABSTRACT

The purpose of the present invention is to provide a novel amide alcohol that can be used as a cosmetic base ingredient. An amide alcohol represented by formula (I).

7 Claims, 2 Drawing Sheets

(56) References Cited

FOREIGN PATENT DOCUMENTS

WO     WO 98/027953 A1    7/1998
WO     WO 99/21825 A1    5/1999

OTHER PUBLICATIONS

EP 17810351.1, Apr. 17, 2020, Partial Supplementary European Search Report.
Indian Hearing Notice issued in Application No. IN 201817049293, dated Jul. 10, 2020. 3 pages.
EP 17810351, Jan. 17, 2020, Extended European Search Report.

[Fig. 1]
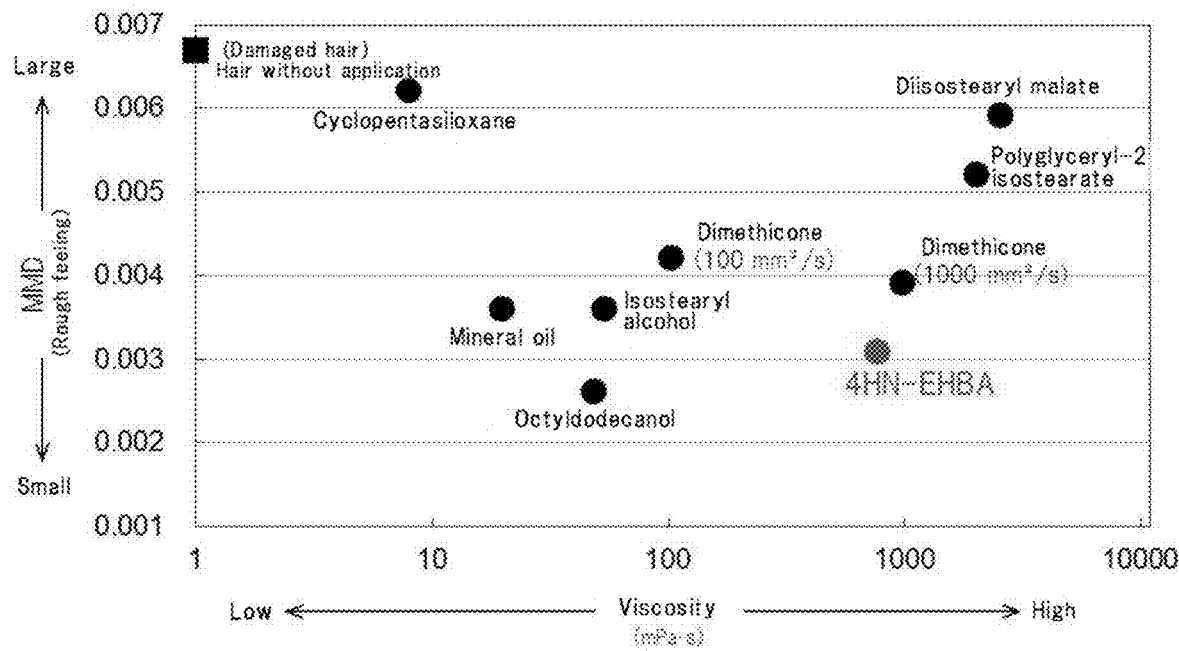
[Fig. 2]
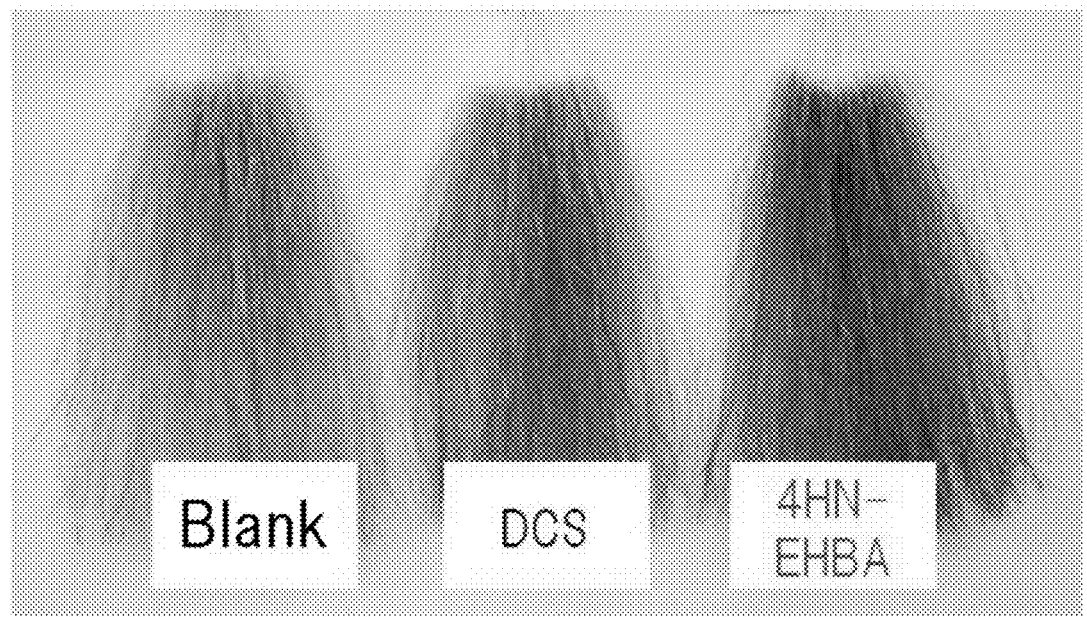

[Fig. 3]
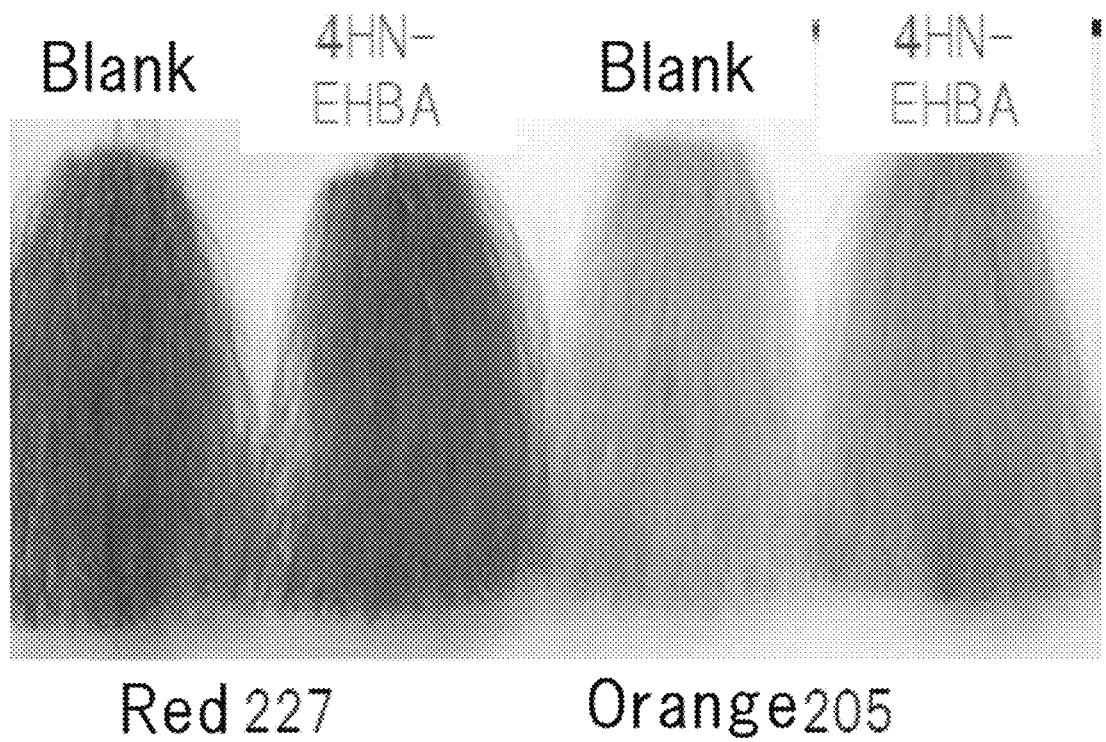

COSMETIC BASE INCLUDING AMIDE ALCOHOL, AND COSMETIC

RELATED APPLICATION

This application is a national stage filing under 35 U.S.C. § 371 of International Patent Application Serial No. PCT/JP2017/021154, filed Jun. 7, 2017, the contents of which is incorporated herein by reference in its entirety.

TECHNICAL FIELD

The present invention relates to a cosmetic base and a cosmetic product comprising an amide alcohol.

BACKGROUND ART

As higher alcohols used for cosmetic base applications, typical examples include isostearyl alcohol, octyldodecanol and oleyl alcohol in liquid form, as well as cetanol, stearyl alcohol and behenyl alcohol in solid form, etc. Both liquid and solid forms are widely used for cosmetic bases for skin care, hair care, and make-up cosmetics and the like.

Meanwhile, since existing nitrogen-containing compounds generally have poor odor, there are few examples in which they are used as a general cosmetic base. For example, an amino acid ester is known as a gelling agent for an oil agent (Patent Document 1), and an N-long chain acyl acidic amino acid ester has been known as a compound having emollient providing power and emulsifying power (Patent Document 2). Since these compounds have ester bonds, they tend to undergo hydrolysis, and there are problems of odor and deterioration of quality due to heating and aging. Therefore, in order to prevent decomposition and prolong the quality, refrigeration is necessary, and consideration must be given to the storage method.

In addition, an amide compound is known as an antibacterial active substance, and while its use in deodorant, dandruff prevention and anti-acne formulations and the like have been examined (Patent Document 3), its use as a cosmetic base has not yet been examined.

CITATION LIST

Patent Document

[Patent Document 1] JP A 2002-316971
[Patent Document 2] JP A H07-118290
[Patent Document 3] US Patent application 2008/0145320

DISCLOSURE OF INVENTION

Problems to be Solved by the Invention

As described above, while nitrogen-containing compounds have not been sufficiently examined as a cosmetic base, the present inventors have carried out extensive research from the viewpoint that application of the nitrogen-containing compounds, which are expected to be suitable for human body, to cosmetic bases should be considered. Accordingly, the problem to be solved by the present invention is to provide a nitrogen-containing compound which is free from the conventional problem of decomposition and is suitable for use in cosmetic products, and a cosmetic base containing thereof.

Means for Solving the Problems

During extensive research to solve the above problem, the present inventors have focused attention on amide alcohols which have not been noticed as a cosmetic base component until now, and have discovered that the amide alcohols have various excellent properties as a cosmetic base component; as a result of further research, the inventors have completed the present invention.

That is, the present invention relates to [1] to [10] below.

[1]

A cosmetic base comprising a compound represented by formula (I):

[Formula 1]

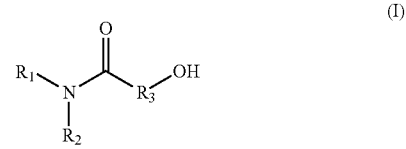

wherein $R_1$ is an optionally substituted C6-C22 hydrocarbon group,
$R_2$ is H, or an optionally substituted C6-C22 hydrocarbon group,
$R_3$ is an optional: substituted, linear or branched C2-C21 hydrocarbon group.

[2]

The cosmetic base according to [1], where $R_1$ is a linear or branched C10-C22 hydrocarbon group; or a cyclic C6-C22 hydrocarbon group; or a benzyl group or a phenylethyl group.

[3]

A thickener or a gelling agent comprising a compound represented by formula (I):

[Formula 2]

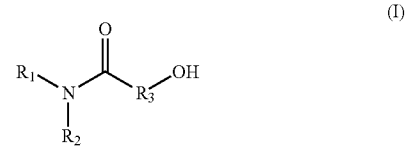

wherein $R_1$ is an optionally substituted C6-C22 hydrocarbon group,
$R_2$ is H, or an optionally substituted C6-C22 hydrocarbon group,
$R_3$ is an optionally substituted, linear or branched C2-C21 hydrocarbon group.

[4]

A humectant comprising a compound represented by formula (I):

[Formula 3]

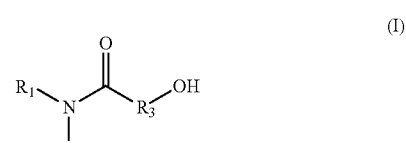

wherein
R₁ is an optionally substituted C6-C22 hydrocarbon group,
R₂ is H, or an optionally substituted C6-C22 hydrocarbon group,
R₃ is an optionally substituted, linear or branched C2-C21 hydrocarbon group.

[5]

A hair dye improving agent comprising a compound represented by formula (I):

[Formula 4]

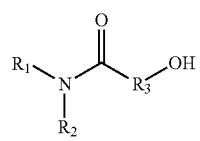

(I)

wherein
R₁ is an optionally substituted C6-C22 hydrocarbon group,
R₂ is H, or an optionally substituted C6-C22 hydrocarbon group,
R₃ is an optionally substituted, linear or branched C2-C21 hydrocarbon group.

[6]

A cosmetic product comprising a compound represented by formula (I):

[Formula 5]

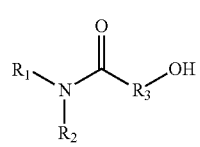

(I)

wherein
R₁ is an optionally substituted C6-C22 hydrocarbon group,
R₂ is H, or an optionally substituted C6-C22 hydrocarbon group,
R₃ is an optionally substituted, linear or branched C2-C21 hydrocarbon group.

[7]

The cosmetic product according to [6], which does not comprise an antibacterial agent comprising a compound represented by formula (I).

[8]

The cosmetic product according to [6] or [7], which is for hair dyeing.

[9]

The cosmetic product according to [6] or [7], comprising an oil agent.

[10]

The cosmetic product according to any one of [6] to [9], comprising 0.1 to 50.0 wt % of a compound represented by formula (I).

Furthermore, the present invention also relates to (1) to (10) below.

(1)

A cosmetic base comprising a compound represented by the above formula (I), which is selected from the group consisting of a thickener, a gelling agent, a humectant and a hair dye improving agent.

(2)

The cosmetic base according to (1), wherein $R_1$ is a linear or branched C10-C22 hydrocarbon group; or a cyclic C6-C22 hydrocarbon group; or a benzyl group or a phenylethyl group.

(3)

The cosmetic base according to (1) or (2), which is a thickener or a gelling agent.

(4)

The cosmetic base according to (1) or (2), which is a humectant.

(5)

The cosmetic base according to (1) or (2), which is a hair dye improving agent.

(6)

A cosmetic product, comprising a compound represented by the above formula (I) as a thickener, a gelling agent, a humectant or a hair dye improving agent.

(7)

The cosmetic product according to (6), comprising a dye.

(8)

The cosmetic product according to (6) or (7), which is for hair dyeing.

(9)

The cosmetic product according to any one of (6) to (8), comprising an oil agent.

(10)

The cosmetic product according to any one of (6) to (9), comprising 0.1 to 50.0 wt % of a compound represented by the formula (I).

Advantageous Effects of Invention

The present invention provides an amide alcohol that can be used as a cosmetic base. Although the amide alcohols of the present invention are compounds having nitrogen, the problem of generation of odor due to decomposition, in particular decomposition during long-term storage at room temperature, is improved as compared with conventional nitrogen-containing compounds; and by utilizing respective characteristics, the amide alcohols can be widely used as a cosmetic base for aqueous cosmetic bases (for example cosmetic lotion and skin cream, etc.) and oily cosmetic bases (for example, hair oil, etc.).

In addition, the amide alcohols of the present invention are relatively easy to purify, and impurities such as odorous ingredients can be removed and a high purity cosmetic base with little odor can be provided.

BRIEF DESCRIPTION OF DRAWINGS

FIG. 1 is a diagram showing the results of evaluation of rough feeling on the hair of liquid amide alcohol and each oil agent.

FIG. 2 is a photograph showing hair dyeing properties of amide alcohol.

FIG. 3 is a photograph showing hair dyeing properties of amide alcohol.

DESCRIPTION OF EMBODIMENTS

An amide alcohol of the present invention is represented by the following formula (I):

[Formula 6]

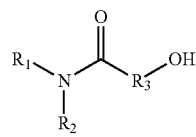

(I)

wherein
$R_1$ is an optionally substituted C6-C22 hydrocarbon group,
$R_2$ is H, or an optionally substituted C6-C22 hydrocarbon group,
$R_3$ is an optionally substituted, linear or branched C2-C21 hydrocarbon group.

As used herein, the term "hydrocarbon group" may be, unless otherwise specified, saturated or unsaturated, linear, branched or cyclic, or a combination of linear or branched with cyclic, and includes a hydrocarbon group consisting of a linear or branched hydrocarbon moiety such as benzyl group, phenylethyl group, etc. and a cyclic hydrocarbon moiety.

That is, the C6-C22 hydrocarbon group in $R_1$ and $R_2$ includes a linear, branched or cyclic C6-C22 hydrocarbon group, or a C6-C22 hydrocarbon group consisting of a linear or branched hydrocarbon moiety and a cyclic hydrocarbon moiety, and examples thereof include cyclic groups such as cyclohexyl, decahydronaphthyl, tetrahydrodicyclopentadiene, sterol, phenyl, naphthyl, anthracenyl, etc.; branched alkyl groups such as ethylhexyl, isostearyl, octyldodecyl, etc.; multibranched alkyl groups such as dimethyl, trimethyl, tetramethyl, etc.; linear alkyl groups such as hexyl, octyl, lauryl, myristyl, cetyl, stearyl, arachyl, behenyl, etc.; and alkenyl groups such as oleyl and elaidyl, etc.

In one embodiment of the invention, $R_1$ is preferably cyclohexyl, ethylhexyl, octyl, lauryl, myristyl, stearyl, oleyl, benzyl or phenylethyl.

In one embodiment of the present invention, $R_2$ is preferably H.

The hydrocarbon group in $R_3$ is a linear or branched C2-C21 hydrocarbon group having no cyclic structure, and examples thereof include alkyl groups such as propyl, butyl, pentyl, hexyl, heptyl, octyl, ethylhexyl, etc., and alkenyl groups such as butylene, pentylene, hexylene, heptylene, etc.

In one embodiment of the present invention, $R_3$ is preferably propylene, butylene, pentylene or hexylene.

In the present invention, each hydrocarbon group may be substituted, and may be substituted with, for example, a hydroxy group, a carboxy group, an aldehyde group.

Examples of substituted C6-C22 hydrocarbon group in $R_1$ and $R_2$ include hexanol, ethylcyclohexanol, hexanoic acid.

Examples of substituted C2-C21 hydrocarbon group in $R_3$ include hydroxybutyl, butyl ketone.

In the compound of the present invention, from the viewpoint of odor, it is important that the carbon number of $R_1$ is 6 or more; when this number is small, the compound has strong odor and is not suitable for use in cosmetic products.

In one embodiment of the present invention, from the viewpoint of odor, $R_1$ is an optionally substituted, saturated or unsaturated, linear, branched or cyclic C6-C22 hydrocarbon group, more preferably $R_1$ is an optionally substituted, saturated or unsaturated, linear or branched C6-C22 hydrocarbon group, or an optionally substituted, saturated cyclic C6-C22 hydrocarbon group. In one embodiment of the present invention, from the viewpoint of odor, it is preferable that the compound of formula (I) does not comprise a benzene ring.

In one embodiment of the present invention, it is preferred that $R_1$ is a linear or branched C10-C22 hydrocarbon group; or a cyclic C6-C22 hydrocarbon group; or a benzyl group or a phenylethyl group.

In a particular embodiment of the invention, from the viewpoint of odor, the compound of formula (I) is not 4-hydroxy-N-octyl, butyramide.

Amide alcohols can be prepared using known synthetic methods.

Examples include:
aminolysis reaction of acid chloride and amine (Schotten-Baumann reaction),
aminolysis reaction of fatty acid anhydride and amine,
aminolysis reaction of methyl ester and amine,
aminolysis reaction of fatty acid and amine,
aminolysis reaction of lactone and amine,
and the like.

Since the aminolysis reaction using lactone and amine does not require the use of a catalyst and the like for the reaction, it is possible to obtain a mixture of safe products suitable for cosmetic bases.

Examples of lactones used for the synthesis of amide alcohol include butyrolactone and caprolactone, examples of amines include cyclohexylamine, 2-ethylhexylamine, octylamine, laurylamine, myristylamine, oleylamine, stearylamine, di-2-ethylhexylamine, benzylamine, phenylethylamine.

In addition, in the case of aminolysis reaction using an amine such as ethanolamine, isopropanolamine, etc., since the ingredients are already used as a cosmetic base, a safer cosmetic product can be provided.

<Cosmetic Base>

The present invention provides a cosmetic base comprising the compound represented by formula (I).

In the present specification, the term "cosmetic base" refers to a component (base material) that provides basic shape and performance for a cosmetic product, and examples thereof include an oil agent, a gelling agent, a thickener, etc.; however, it is not an additive that imparts additional functions, such as active components including antibacterial agent.

The cosmetic base in the present specification can be either a composition consisting essentially of one or more compounds of formula (I), or a composition further comprising other cosmetic components.

In one embodiment of the present invention, the cosmetic base is a composition comprising, in addition to the compound of formula (I), other cosmetic base components usually used to provide a specific shape to cosmetic products.

Other cosmetic bases include, but are not limited to, solid oils and fats, liquid oils, gelling agents, thickeners, and silicone oils, silicone derivatives, surfactants, water, etc. other than the amino alcohols of the formula (I) of the present invention.

The cosmetic base of the present invention can be used for producing various cosmetic products.

The cosmetic product of the present invention comprises one or more compounds of formula (I).

In the present specification, the term "cosmetic product" means any product that is applied to the skin, hair, lips, etc. for the purpose of cleaning the body or beautifying the appearance, although not particularly limited thereto. Specific examples include, but are not limited to, skin care products, makeup products, hair care products, body care products, etc.

Examples of skin care products include, but are not limited to, lotion, cream, milky lotion, gel, beauty essence, cosmetic oil, pack, cleansing, face cleanser, whitening cosmetics, UV care cosmetics, etc.

Examples of makeup products include, but are not limited to, makeup base, foundation, lip color, lipstick, lip cream, lip gloss, cheek color, eyeliner, mascara, eye shadow, eyebrow, etc.

Examples of hair care products include, but are not limited to, shampoo, conditioner, hair rinse, hair treatment, hair styling agent, permanents, hair color, etc.

Examples of body care products include, but are not limited to, body shampoo, body lotion, hand cream, nail cream, deodorant cosmetics, etc.

In one embodiment of the present invention, the cosmetic product is a cosmetic product not comprising an antibacterial agent.

In another embodiment of the present invention, the cosmetic product does not comprise an antibacterial agent comprising a compound of formula (I).

Since the compound of formula (I) has moisture retention and adhesion properties, it is suitable for use in cosmetic products requiring moisture retention and adhesion properties. In one embodiment of the present invention, the compound of formula (I) can also be used as a humectant/adhesive for cosmetic products.

The present invention also provides a moisturizing cosmetic product comprising the compound of formula (I) as a moisturizing active component.

The compound of formula (I) is suitable for use in cosmetic products comprising an oil agent, such as cleansing oils, hair treatments and skin creams, because of its excellent compatibility with oil agents.

In addition, the compound of formula (I) is suitable for use in semisolid or solid cosmetic products comprising an oil agent, since it has the ability to thicken and gelate oil agents. In one embodiment of the present invention, the compound of formula (I) can also be used as a thickener/gelling agent for cosmetic products.

Examples of oil agents used with the compound of formula (I) include glycerin; ethanol; higher alcohols such as octyldodecanol and isostearyl alcohol, etc.; ester oils such as isotridecyl isononanoate, octyldodecyl myristate, triethylhexanoin, diisostearyl malate, etc.; hydrocarbon oils such as squalane, mineral oil, hydrogenated polyisobutene, etc.; and silicone oils such as dimethicone and cyclopentasiloxane, etc.

In a preferred embodiment of the present invention, in order to produce oil-based cosmetic products, the compound of formula (I) is blended in a cosmetic product at 0.1 to 90 wt %, preferably 0.5 to 85 wt %, more preferably 1.0 to 80 wt %.

In a preferred embodiment of the invention, in order to produce thickened or gelled cosmetic products, the compound of formula (I) is blended in a cosmetic product at 0.1 to 50.0%, preferably 0.5 to 40.0%, more preferably 1.0 to 30.0%.

In one embodiment of the present invention, in order to obtain a cosmetic product with soft texture, 0.1 to 20.0%, preferably 0.5 to 15.0% of the compound of formula (I) is preferably used as a gelling agent for the oil agent.

In another embodiment of the present invention, in order to obtain a cosmetic product with hard texture, 5.0 to 30.0%, preferably 7.0 to 25.0% of the compound of formula (I) is preferably used as a gelling agent for the oil agent.

Since the compound of formula (I) is excellent in texture improving property, it is suitable for use in any cosmetic products for application to lips, skin, hair and the like. In one embodiment of the present invention, the compound of formula (I) can also be used as a texture improving agent for cosmetic products.

In a preferred embodiment of the present invention, in order to improve the texture of a cosmetic product, 1.0 to 80.0%, preferably 5.0 to 70.0% of the compound of formula (I) is blended.

Since the compound of formula (I) has an effect of imparting hair dyeing properties, it is suitable for use in hair dyeing cosmetics. In one embodiment of the present invention, the compound of formula (I) can also be used as a hair dye improving agent. Since the compound of the formula (I) has a nitrogen atom, the compound is considered to be excellent in adhering a dye.

Accordingly, the present invention also provides a cosmetic product containing a compound of formula (I) and a dye, in particular a hair dyeing cosmetic product. In a preferred embodiment of the present invention, in order to improve hair dyeing properties of hair dye cosmetics, the compound of formula (I) is blended in an amount of 0.1 to 30.0%, preferably 0.5 to 25.0%, more preferably 1.0 to 20.0%.

Since the compound of formula (I) has various forms such as a liquid and a solid at room temperature, it can be utilized in various cosmetic products utilizing such property.

The form of the cosmetic product is not particularly limited, and it may be solid, liquid, milky lotion, cream, gel and the like. Those skilled in the art can appropriately select an amide alcohol suitable for a desired shape.

The blending amount of the compound of formula (I) in a cosmetic product varies depending on the type of desired cosmetic product and other materials to be combined, and it can be appropriately adjusted by those skilled in the art.

In one embodiment of the present invention, the cosmetic product comprises 0.1 to 90 wt %, preferably 2 to 50 wt %, more preferably 10 to 30 wt % of the compound of formula (I).

When the cosmetic product is a makeup product, the makeup product comprises 2 to 80 wt %, preferably 5 to 75 wt %, more preferably 10 to 70 wt % of the compound of formula (I).

When the cosmetic product is a lipstick, the lipstick comprises 5 wt % or more, preferably 10 wt % or more, more preferably 15 wt % or more of the compound of formula (I).

When the cosmetic product is a hair care product, the hair care product comprises 1 to 90 wt %, preferably 5 to 80 wt %, more preferably 10 to 70 wt % of the compound of formula (I).

When the cosmetic product is a hair oil, a hair cream or a hair styling agent, the hair oil, hair cream or hair styling agent comprises 1 to 80 wt %, preferably 3 to 70 wt %, more preferably 5 to 60 wt % of the compound of formula (I).

When the cosmetic product is a skin care product, the skin care product comprises 0.1 to 90 wt %, preferably 0.5 to 85 wt %, more preferably 1.0 to 80 wt % of the compound of formula (I).

When the cosmetic product is a skin cream, a cosmetic oil or an UV care cosmetic, the skin cream, cosmetic oil or UV care cosmetic comprises 0.1 to 80 wt %, preferably 0.5 to 70 wt %, more preferably 1 to 60 wt % of the compound of formula (I).

When the cosmetic product is a cleansing, the cleansing comprises 0.1 to 80 wt %, preferably 0.5 to 75 wt %, more preferably 1 to 70 wt % of the compound of formula (I).

When the cosmetic product is a body care product, the body care product comprises 0.1 to 80 wt %, preferably 0.5 to 70 wt %, more preferably 1 to 60 wt % of the compound of formula (I).

Cosmetic products can be produced by a known method of producing a cosmetic product. For example, they can be obtained by dissolving a cosmetic base component under stirring to obtain a uniform mixture, then adding an additive such as a perfume, and molding.

In one embodiment of the present invention, there is provided a method of producing a cosmetic product, comprising adding a compound of formula (I).

In one embodiment of the present invention, there is provided a method of producing a cosmetic product, comprising adding a compound of formula (I) to thicken or gelate.

In one embodiment of the present invention, the addition of the compound of formula (I) can improve the texture of cosmetic products. In a preferred embodiment of the present invention, by adding the amide alcohol of the present invention, a smooth texture (feeling of use/feeling of application) is provided to cosmetic products.

Accordingly, in one embodiment of the present invention, there is provided a method of improving the texture of a cosmetic product comprising adding a compound of formula (I).

Hereinafter, the present invention will be described in more detail based on the working examples, but the present invention is not limited to these examples, and various modifications may be made without departing from the technical idea of the present invention. In the present specification, unless otherwise specified, % means wt %.

WORKING EXAMPLE

Synthetic Example 1 4HN-CHBA

Synthesis of 4-hydroxy-N-cyclohexyl, butyramide

[Formula 7]

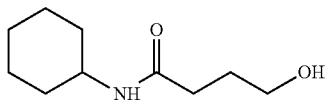

An excess amount of butyrolactone was added and mixed to 591 g of cyclohexylamine, and the mixture was heated to 130° C. and maintained for 8 hours. Thereafter, it was cooled to room temperature to obtain 1134 g (yield 95%) of a white solid.

After the reaction, purification was carried out by drying and deodorization to obtain an amide alcohol having a purity of 99%.

Synthetic Example 2 4HN-EHBA 4-hydroxy-N-2-ethylhexyl, butyramide

[Formula 8]

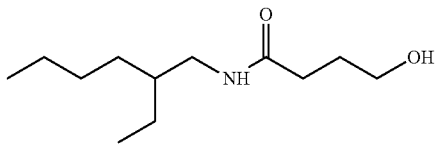

An excess amount of butyrolactone was added and mixed to 400 g of 2-ethylhexylamine, and the mixture was heated to 130° C. and maintained for 8 hours. Thereafter, it was cooled to room temperature to obtain 666 g of a colorless liquid (yield 78%).

After the reaction, purification was carried out by drying and deodorization to obtain an amide alcohol having a purity of 99%.

Synthetic Example 3 4HN-OBA

Synthesis of 4-hydroxy-N-octyl, butyramide

[Formula 9]

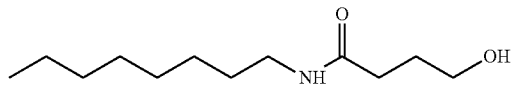

An excess amount of butyrolactone was added and mixed to 399 g of n-octylamine, and the mixture was heated to 130° C. and then cooled to room temperature to obtain 873 g of a white solid (yield 89%).

After the reaction, purification was carried out by drying and deodorization to obtain an amide alcohol having a purity of 99%.

Synthetic Example 4 4HN-LBA

Synthesis of 4-hydroxy-N-lauryl, butyramide

[Formula 10]

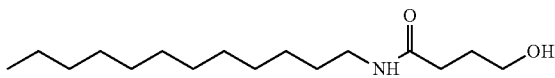

An excess amount of butyrolactone was added and mixed to 406 g of laurylamine, and the mixture was heated to 130° C. and maintained for 8 hours. Thereafter, it was cooled to room temperature to obtain 700 g of a slightly yellow solid (yield 84%).

After the reaction, purification was carried out by drying and deodorization to obtain an amide alcohol having a purity of 99%.

Synthetic Example 5 4HN-MBA

Synthesis of 4-hydroxy-N-myristyl, butyramide

[Formula 11]

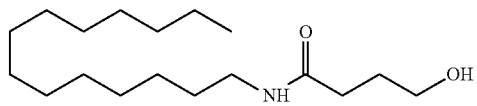

An excess amount of butyrolactone was added and mixed to 213 g of myristylamine, and the mixture was heated to 130° C. and maintained for 8 hours. Thereafter, it was cooled to room temperature to obtain 427 g of a white solid (yield 75%).

After the reaction, purification was carried out by drying and deodorization to obtain an amide alcohol having a purity of 99%.

Synthetic Example 6 4HN-OLBA

Synthesis of 4-hydroxy-N-oleyl, butyramide

[Formula 12]

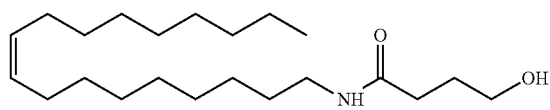

An excess amount of butyrolactone was added and mixed to 343 g of oleylamine, and the mixture was heated to 100° C. and maintained for 8 hours. Thereafter, it was cooled to room temperature to obtain 425 g of a yellow solid (yield 94%).

After the reaction, purification was carried out by drying and deodorization to obtain an amide alcohol having a purity of 99%.

Synthetic Example 7 4HN-STBA

Synthesis of 4-hydroxy-N-stearyl, butyramide

[Formula 13]

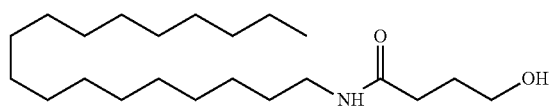

An excess amount of butyrolactone was added and mixed to 387 g of stearylamine, and the mixture was heated to 130° C. and maintained for 8 hours. Thereafter, it was cooled to room temperature to obtain 445 g of a slightly yellow solid (yield 87%).

After the reaction, purification was carried out by drying and deodorization to obtain an amide alcohol having a purity of 99%.

Synthetic Example 8 6HN-LHA

Synthesis of 6-hydroxy-N-lauryl, hexylamide

[Formula 14]

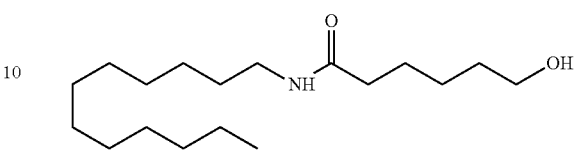

To 294 g of laurylamine, an excess amount of caprolactone and NaOMe as a catalyst were added and mixed. The mixture was heated to 130° C. and maintained for 1 hour. Thereafter, it was cooled to room temperature to obtain 454 g of a white solid (yield 95%).

After the reaction, purification was carried out by washing with water, drying and deodorization to obtain an amide alcohol having a purity of 99%.

Comparative Example 1

4-hydroxy-N-butyl, butyramide (4HN-BuBA)

[Formula 15]

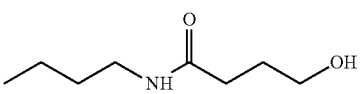

An excess amount of butyrolactone was added and mixed to 100 g of butylamine, and the mixture was heated to 100° C. and maintained for 8 hours. Thereafter, it was cooled to room temperature to obtain 152 g of a yellow solid (yield 70%).

After the reaction, purification was carried out by drying and deodorization to obtain an amide alcohol having a purity of 99%.

Odor of the ingredient amine is strong and it is hard to handle. In addition, the odor of the target substance is also strong and it is unsuitable for use as a cosmetic product.

Comparative Example 2

4-hydroxy-N-lignoceryl, butyramide (4HN-LigBA)

[Formula 16]

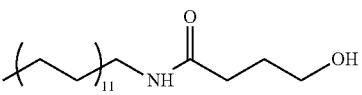

An excess amount of butyrolactone was added and mixed to 70 g of lignocerylamine, and the mixture was heated to 140° C. and maintained for 8 hours. Thereafter, the mixture was cooled to room temperature to obtain 71 g of a yellow solid (yield 82%).

After the reaction, purification was carried out by drying and deodorization to obtain an amide alcohol having a purity of 93%.

The melting point of the target substance is high (around 90° C.) and it is difficult to handle. Since the boiling point of the ingredient amine is high, purification is difficult, and the odor of the mixture is strong and it is unsuitable for use as a cosmetic product.

Comparative Example 3

N,N-1,2-ethanediylbis-4-hydroxy, butanamide (EDHBA)

[Formula 17]

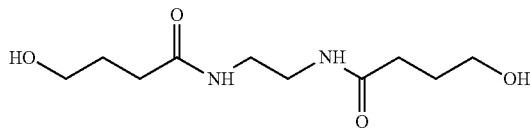

An excess amount of butyrolactone was added and mixed to 40 g of ethylenediamine, and the mixture was heated to 150° C. and maintained for 8 hours. Thereafter, it was cooled to room temperature to obtain 71 g of a yellow solid (yield 89%).

After the reaction, purification was carried out by drying to obtain an amide alcohol having a purity of 93%.

The melting point of the target substance is as high as around 100° C., so that ordinary purification cannot be carried out and removal of monomers is difficult. Therefore, the odor of the mixture is strong and it is unsuitable for use as a cosmetic product.

Physical property values of the amide alcohols obtained in Synthetic examples 1 to 8 are shown below.

In the present specification, each amide alcohol is represented using the following abbreviations Synthetic example 1: "4HN-CHBA" (4-hydroxy-N-cyclohexyl, butyramide)
Synthetic example 2: "4HN-EHBA" (4-hydroxy-N-2-ethylhexyl, butyramide)
Synthetic example 3: "4HN-OBA" (4-hydroxy-N-octyl, butyramide)
Synthetic example 4: "4HN-LBA" (4-hydroxy-N-lauryl, butyramide)
Synthetic example 5: "4HN-MBA" (4-hydroxy-N-myristyl, butyramide)
Synthetic example 6: "4HN-OLBA" (4-hydroxy-N-oleyl, butyramide)
Synthetic example 7: "4HN-STBA" (4-hydroxy N stearyl, butyramide)
Synthetic example 8: "6HN-LHA" (6-hydroxy-N-lauryl, hexylamide)

<Evaluation of Solubility and Gelling Ability>

The amide alcohol and each liquid were heated and mixed, and the critical gelation concentration was measured by sample tube inversion method.

Sample tube used: used tube: Maruemu screw tube No. 7 (trunk diameter 35 mm, total length 78 mm)

The results are shown in Table 1 below.

TABLE 1

Evaluation results of solubility and gelling ability with amide alcohols

| Name<br>Property | 4HN-CHBA<br>Solid | 4HN-EHBA<br>Liquid | 4HN-OBA<br>Solid | 4HN-LBA<br>Solid | 4HN-MBA<br>Solid | 4HN-OLBA<br>Solid | 4HN-STBA<br>Solid | 6HN-LHA<br>Solid |
|---|---|---|---|---|---|---|---|---|
| Water | S | I | S | EG<br>15 g/L(1.5 wt %) | EG<br>21 g/L(2.1 wt %) | I | I | I |
| Glycerin | T<br>(≥12 wt %) | S | G<br>15 g/L(1.2 wt %) | G<br>25 g/L(2.0 wt %) | I | I | I | I |
| Ethanol | S | S | S | S | S | S | I | S |
| Octyldodecanol | T<br>(≥18 wt %) | S | S | G<br>75 g/L(9.0 wt %) | G<br>50 g/L(6.0 wt %) | S | G<br>19 g/L(2.2 wt %) | G<br>50 g/L(6.0 wt %) |
| Octyldodecyl myristate | I | S | G<br>75 g/L(7.9 wt %) | G<br>30 g/L(3.2 wt %) | G<br>19 g/L(2.0 wt %) | G<br>25 g/L(2.6 wt %) | G<br>7.5 g/L(0.8 wt %) | G<br>12 g/L(1.2 wt %) |
| Triethylhexanoin | I | I | G<br>38 g/L(3.5 wt %) | G<br>25 g/L(2.4 wt %) | G<br>4.8 g/L(0.5 wt %) | G<br>14 g/L(1.3 wt %) | G<br>7.5 g/L(0.7 wt %) | G<br>7.9 g/L(0.7 wt %) |
| Squalane | I | I | I | G<br>150 g/L(17 wt %) | G<br>21 g/L(2.5 wt %) | G<br>13 g/L(1.4 wt %) | G<br>10 g/L(1.1 wt %) | G<br>14 g/L(1.5 wt %) |

S: Soluble,
I: Insoluble/separation,
G: Gel,
T: Thickening,
EG: Emulsion gel,
Number: Critical gelation concentration.

It was confirmed that 4HN-CHBA thickened glycerin, and 4HN-OBA and 4HN-LBA gelled glycerin.

In the prior art, thickening and gelation of glycerin is carried out using magnesium carbonate as a gelling agent, or using a peptide-based gemini type amphiphilic compound. When gelling glycerin and oil agent using a peptide-based gemini type amphiphilic compound, there were problems that the work process to complete gelation was troublesome, etc.; however, in the case of using an amide alcohol, gelation can be carried out by mixing the amide alcohol with each oil agent or glycerin, melting by heating, and then cooling; and this is extremely simple.

Furthermore, regarding the amide alcohols other than 4HN-CHBA and 4HN-EHBA, it was confirmed that saturated branched alcohols, esters (diesters, triesters) and hydrocarbon oils (squalane) are gelled.

TABLE 2

Solubility of glycerin with various alcohols

| Blending amount of each oil agent (80 wt %) | Blending amount of glycerin (20 wt %) | | | |
|---|---|---|---|---|
| | 4HN-EHBA | Ethanol | Octyldodecanol | Isostearyl alcohol |
| State at 25° C. (1 week after) | C | C | N | N |

C: Soluble,
N: Insoluble

4HN-EHBA can be dissolved in glycerin, and has quite unique properties in oily cosmetic ingredients currently on the market.

There are isostearyl alcohol and octyldodecanol as a saturated alcohol (liquid) with multiplicity of uses, but they do not have solubility with glycerin; 4HN-EHBA can be used as an alcohol with higher multiplicity of uses.

4HN CHBA and 4HN-OBA were confirmed to have solubility in water, thickening/gelation with glycerin.

4HN-LBA is emulsification-gelled with water, and gelled with glycerin.

Furthermore, since the above 4HN-OBA and 4HN-LBA are confirmed to be gelled also with an ester oil, it has been found that they have wide relation with from water to oils.

<Texture Improving Effect on Hair>
Human hair strand BS-B3N (100% black hair, root aligning II, Beaulax Co., Ltd.) was damage-treated by the method prescribed by our company, to make damaged hair.
Approximately 0.2 mL of an oil agent was added dropwise to the dry damaged hair, and uniformly applied using a spatula.
100 damaged hairs were arranged in a width of 1 cm as evenly as possible, and MMD was measured using friction tester KES-SE (Kato Tech Co., Ltd.).
MMD: Variable value of friction coefficient. As the MMD value decreases, fluctuation of friction coefficient is small and roughness is small, so the smoothness is good.
FIG. 1 shows a diagram of measured values.

4HN-EHBA has a viscosity of about 770 mPa·s and is a slightly viscous liquid oil. Generally, oil agents having high viscosity on the hair have a tendency to have large rough feeling; however, 4HN-EHBA exhibits an effect to reduce rough feeling on the hair even compared to oil agents having low viscosity (for example, mineral oils with multiplicity of uses as a hair oil and isostearyl alcohol that is a liquid higher alcohol).

<Evaluation of Hair Dyeing Properties A>
Acid hair dye of the following formulation was prepared and used to dye the hair.

TABLE 3

Acid hair dye, formulation for evaluation

| | Product name/ Cosmetic labeling name | wt % | |
|---|---|---|---|
| 1 | Ethanol | 15.0 | |
| 2 | Haiaqueouster-DCS | 5.0 | — |
| | 4HN-EHBA | — | 5.0 |
| 3 | Glycos ™ Clear 70 (Glycolic acid) | 5.0 | |

TABLE 3-continued

Acid hair dye, formulation for evaluation

| | Product name/ Cosmetic labeling name | wt % |
|---|---|---|
| 4 | HEC Deicel SE900 (hydroxyethyl cellulose) | 2.0 |
| 5 | Black 401 | 0.5 |
| 6 | Water | 72.5 |

*In the blank, oil agent is replaced with water
*Haiaqueouster DCS (bis-ethoxydiglycol succinate, Kokyu Alcohol Kogyo Co., Ltd.)

The hair dyed with each acid hair dye is shown in FIG. 2.

The hair dyeing properties were visually evaluated. The results are shown in Table 4 below.

<Evaluation Criteria>
5: Very good hair dyeing properties
4: Good hair dyeing properties
3: Sightly good hair dyeing properties
2: Hair dyeing properties are recognized
1: Poor hair dyeing properties

TABLE 4

Evaluation of hair dyeing properties

| | 5-grades evaluation |
|---|---|
| Blank | 2 |
| Haiaqueouster DCS | 3 |
| 4HN-EHBA | 4 |

In comparison with non-blending (blank) and in comparison with Haiaqueouster DCS, the amide alcohol was confirmed to be excellent in hair dyeing properties.

<Evaluation of Hair Dyeing Properties B>
In the formulation shown in Table 3, the hair dyeing properties of the blank and the amide alcohol were compared, while replacing Black 401 (CI 20470) with Red 227 (CI 17200) or Orange 205 (CI 15510).

The dyed hair is shown in FIG. 3.

The hair dyeing properties were visually evaluated. The respective results are shown in Table 5 and Table 6 below.

TABLE 5

Evaluation of hair dyeing properties (Red 227)

| | 5-grades evaluation |
|---|---|
| Blank | 2 |
| 4HN-EHBA | 3 |

TABLE 6

Evaluation of hair dyeing properties (Orange 205)

| | 5-grades evaluation |
|---|---|
| Blank | 2 |
| 4HN-EHBA | 4 |

Below, using amide alcohols, formulation examples of cosmetic products such as make-up products, skin care products, hair care products, etc. are shown.

TABLE 7

① Skin cream

| | | |
|---|---|---|
| [Oil phase] | Triethylhexanoin | 4.00 |
| | Mineral oil | 4.00 |
| | 4HN-STBA | 3.00 |
| | Pentylene glycol | 3.00 |
| | Hydrogenated polyisobutene | 2.00 |
| | Hexyldecyl isostearate | 2.00 |
| | Glyceryl stearate | 1.00 |
| | Stearic acid PEG-100 | 0.50 |
| [Aqueous phase] | Glycerin | 2.00 |
| | (Ammonium acryloyldimethyltaurate/VP) copolymer | 0.22 |
| | Methylparaben | 0.10 |
| | Xanthan gum | 0.08 |
| | Water | 78.10 |
| | Total | 100.00 |

TABLE 8

② Acid hair dye

| | |
|---|---|
| Ethanol | 15.00 |
| 4HN-EHBA | 5.00 |
| Glycolic acid | 5.00 |
| Hydroxyethyl cellulose | 2.00 |
| Pigment | 0.50 |
| Water | 72.50 |
| Total | 100.00 |

TABLE 9

③ Hair oil

| | |
|---|---|
| Isostearyl isostearate | 35.00 |
| Isododecane | 23.00 |
| Triisostearin | 15.00 |
| 4HN-EHBA | 12.00 |
| Ethanol | 6.00 |
| Camellia oil | 6.00 |
| Ethylhexyl methoxycinnamate | 3.00 |
| Total | 100.00 |

INDUSTRIAL APPLICABILITY

As stated above, the compound of formula (I) can be used in a variety of cosmetic formulations.

The invention claimed is:

1. A composition comprising water gelled with 4-hydroxy-N-lauryl, butyramide and/or 4-hydroxy-N-myristyl, butyramide, not comprising an additional thickener.

2. A composition comprising glycerin thickened or gelled with 4-hydroxy-N-cyclohexyl, butyramide, 4-hydroxy-N-octyl, butyramide and/or 4-hydroxy-N-lauryl, butyramide.

3. A moisturizing composition comprising a compound of formula (I):

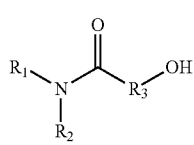

wherein
$R_1$ is cyclohexyl, ethylhexyl, or linear or branched C8-C22 hydrocarbon group,
$R_2$ is H,
$R_3$ is a linear or branched C2-C8 hydrocarbon group, wherein the hydrocarbon group not substituted by a hydroxyl group,
as a humectant ingredient, and
a further cosmetic component, and
not comprising a thickener other than the compound of formula (I).

4. A moisturizing composition comprising a compound of formula (I):

wherein
$R_1$ is a C6-C22 hydrocarbon group which is optionally substituted by hydroxyl group, carboxyl group and/or aldehyde group,
$R_2$ is H, or a C6-C22 hydrocarbon group which is optionally substituted by hydroxyl group, carboxyl group and/or aldehyde group,
$R_3$ is a linear or branched C2-C21 hydrocarbon group, wherein the hydrocarbon group not substituted by a hydroxyl group, and
a further cosmetic component, and
not comprising a surfactant.

5. A cosmetic product for hair dyeing comprising a dye and a compound of formula (I):

wherein
$R_1$ is a C6-C22 hydrocarbon group which is optionally substituted by hydroxyl group, carboxyl group and/or aldehyde group,
$R_2$ is H, or a C6-C22 hydrocarbon group which is optionally substituted by hydroxyl group, carboxyl group and/or aldehyde group,
$R_3$ is a linear or branched C2-C21 hydrocarbon group, wherein the hydrocarbon group is not substituted by a hydroxyl group.

6. The moisturizing composition according to claim 4, wherein
$R_1$ is cyclohexyl, ethylhexyl, or a linear or branched C8-C22 hydrocarbon group,
$R_2$ is H,
$R_3$ is a linear or branched C2-C8 hydrocarbon group, wherein the hydrocarbon group is not substituted by a hydroxyl group.

7. The cosmetic product for hair dyeing according to claim 5, wherein
$R_1$ is cyclohexyl, ethylhexyl, or a linear or branched C8-C22 hydrocarbon group,
$R_2$ is H,
$R_3$ is a linear or branched C2-C8 hydrocarbon group, wherein the hydrocarbon group is not substituted by a hydroxyl group.

* * * * *